US008197406B2

(12) United States Patent
Caduff et al.

(10) Patent No.: US 8,197,406 B2
(45) Date of Patent: Jun. 12, 2012

(54) DEVICE AND METHOD FOR MEASURING A PROPERTY OF LIVING TISSUE

(75) Inventors: Andreas Caduff, Zurich (CH); Stephan Buschor, Zurich (CH); Pascal Truffer, Zurich (CH); Etienne Hirt, Cham (CH); Gianluca Stalder, Thalwil (CH)

(73) Assignee: Biovotion AG, Zurich (CH)

( * ) Notice: Subject to any disclaimer, the term of this patent is extended or adjusted under 35 U.S.C. 154(b) by 1261 days.

(21) Appl. No.: 10/580,209

(22) PCT Filed: Feb. 10, 2004

(86) PCT No.: PCT/CH2004/000077
§ 371 (c)(1),
(2), (4) Date: Sep. 28, 2007

(87) PCT Pub. No.: WO2005/053523
PCT Pub. Date: Jun. 16, 2005

(65) Prior Publication Data
US 2010/0099960 A1    Apr. 22, 2010

(30) Foreign Application Priority Data
Dec. 2, 2003    (WO) .............. PCT/CH03/00795

(51) Int. Cl.
*A61B 5/00*    (2006.01)
*A61B 5/05*    (2006.01)
(52) U.S. Cl. .................. 600/365; 600/345; 600/347
(58) Field of Classification Search .................. 600/347, 600/365, 316
See application file for complete search history.

(56) References Cited

U.S. PATENT DOCUMENTS

| 3,482,167 | A | * | 12/1969 | Hart et al. .................. 455/242.1 |
| 3,803,828 | A | * | 4/1974 | Keeler et al. .................. 368/87 |
| 4,509,531 | A | | 4/1985 | Ward |
| 4,679,426 | A | | 7/1987 | Fuller et al. |
| 4,765,179 | A | | 8/1988 | Fuller et al. |
| 4,875,486 | A | | 10/1989 | Rapoport et al. |
| 5,050,612 | A | | 9/1991 | Matsumura |

(Continued)

FOREIGN PATENT DOCUMENTS
AT    395 075    9/1992
(Continued)

OTHER PUBLICATIONS

English Abstract of AT 395 075 dated Sep. 10, 1992.
(Continued)

*Primary Examiner* — Miranda Le
*Assistant Examiner* — Tiffany Weston
(74) *Attorney, Agent, or Firm* — Ladas & Parry LLP

(57) ABSTRACT

A device for measuring the glucose level in living tissue has electrodes (5, 6) for being brought into contact with the specimen and a voltage-controlled oscillator (31) as a signal source for generating an AC voltage in a given frequency range. The AC voltage is applied to the electrodes (5, 6). A voltage over the electrodes is fed to a processing circuitry (37, 38), which converts it to the glucose level using calibration data. The voltage-controlled oscillator (31) has a symmetric design with adjustable gain for generating signals in a large frequency range with low distortions at a low supply voltage. The processing circuit comprises a simple rectifier network with software-based correction. The electrodes (5, 6) are of asymmetric design and optimized for biological compatibility.

18 Claims, 4 Drawing Sheets

U.S. PATENT DOCUMENTS

| | | | |
|---|---|---|---|
| 5,077,476 A | | 12/1991 | Rosenthal |
| 5,109,855 A | | 5/1992 | Gunter |
| 5,212,817 A | * | 5/1993 | Atkinson ............... 455/161.2 |
| 5,353,802 A | | 10/1994 | Ollmar |
| 5,508,203 A | | 4/1996 | Fuller et al. |
| 5,771,891 A | | 6/1998 | Gozani |
| 5,792,668 A | | 8/1998 | Fuller et al. |
| 5,804,967 A | | 9/1998 | Miller et al. |
| 5,890,489 A | | 4/1999 | Elden |
| 6,028,433 A | | 2/2000 | Cheiky-Zelina et al. |
| 6,175,752 B1 | * | 1/2001 | Say et al. ............... 600/345 |
| 6,182,504 B1 | | 2/2001 | Gaisford |
| 6,309,884 B1 | | 10/2001 | Cooper et al. |
| 6,356,776 B1 | | 3/2002 | Berner et al. |
| 6,517,482 B1 | | 2/2003 | Elden et al. |
| 6,565,509 B1 | | 5/2003 | Say et al. |
| 6,723,048 B2 | | 4/2004 | Fuller |
| 2002/0060613 A1 | * | 5/2002 | Pao et al. ............... 331/177 V |
| 2002/0106709 A1 | | 8/2002 | Potts et al. |
| 2002/0119759 A1 | * | 8/2002 | Hahn ............... 455/77 |
| 2002/0155615 A1 | | 10/2002 | Novikov et al. |
| 2003/0095420 A1 | * | 5/2003 | Imamura ............... 363/21.12 |
| 2003/0098745 A1 | | 5/2003 | Yamashita |
| 2003/0153821 A1 | | 8/2003 | Berner et al. |
| 2004/0039254 A1 | | 2/2004 | Stivoric et al. |
| 2004/0104736 A1 | | 6/2004 | Cohen et al. |
| 2004/0133353 A1 | | 7/2004 | Geutebruck |
| 2004/0147819 A1 | | 7/2004 | Caduff et al. |
| 2004/0240512 A1 | | 12/2004 | Pesach |
| 2005/0101842 A1 | | 5/2005 | Suda |
| 2005/0113662 A1 | | 5/2005 | Kjennati et al. |
| 2006/0264730 A1 | | 11/2006 | Stivoric et al. |

FOREIGN PATENT DOCUMENTS

| | | |
|---|---|---|
| DE | 30 17 168 | 11/1981 |
| DE | 44 46 346 | 6/1996 |
| DE | 100 35 415 | 1/2002 |
| EP | 0 298 441 | 1/1989 |
| EP | 0 309 085 | 3/1989 |
| EP | 0 266 434 | 10/1995 |
| EP | 1 092 386 | 4/2001 |
| GB | 2 033 575 | 5/1980 |
| GB | 2 055 206 | 2/1981 |
| GB | 2 055 206 A | 2/1981 |
| GB | 1 599 241 | 9/1981 |
| GB | 2 100 864 | 1/1983 |
| JP | 62 83649 | 4/1987 |
| JP | 9-201337 | 8/1997 |
| JP | 2000-162176 | 6/2000 |
| JP | 2003-163593 | 6/2003 |
| RU | 2 069 863 | 11/1996 |
| RU | 2 073 242 | 2/1997 |
| RU | 2 088 927 | 8/1997 |
| SU | 1698724 | 12/1991 |
| WO | 85/04481 | 10/1985 |
| WO | 93/18395 | 9/1993 |
| WO | 93/18402 | 9/1993 |
| WO | 95/04496 | 2/1995 |
| WO | 97/39341 | 10/1997 |
| WO | 98/04190 | 2/1998 |
| WO | 98/09566 | 3/1998 |
| WO | 99/39627 | 8/1999 |
| WO | 99/44495 | 9/1999 |
| WO | 00/09996 | 2/2000 |
| WO | 00/43759 | 7/2000 |
| WO | 01/36952 | 5/2001 |
| WO | 01/47415 | 7/2001 |
| WO | 02/062214 | 8/2002 |
| WO | 02/069791 | 9/2002 |
| WO | 02 069791 A | 9/2002 |
| WO | 02/073179 | 9/2002 |
| WO | WO 02/069791 * | 9/2002 |
| WO | 03/017834 | 3/2003 |

OTHER PUBLICATIONS

English Abstract of DE 100 35 415 dated Jan. 31, 2002.
English Abstract of EP 1 092 386 dated Apr. 18, 2001.
Patent Abstracts of Japan of JP 9-201337 dated Aug. 5, 1997.
Patent Abstracts of Japan of JP 2000-162176 dated Jun. 16, 2000.
Patent Abstracts of Japan of JP 62-83649 dated Apr. 17, 1987.
Derwent Abstract of RU 2 069 863 dated Nov. 27, 1996.
English Abstract of RU 2 073 242 dated Feb. 10, 1997.
English Abstract of RU 2 088 927 dated Aug. 27, 1997.
Derwent Abstract of SU 1698724 dated Dec. 15, 1991.
Khalil, O. S. "Non-Invasive Glucose Measurement Technologies: An Update from 1999 to the Dawn of the New Millennium" *Diabetes Technology & Therapeutics* (2002) vol. 6, No. 5, pp. 660-695.
Choleau, C. et al. "Prevention of Hypoglycemia Using Risk Assessment With a Continuous Glucose Monitoring System" *Diabetes* (2002) vol. 51, pp. 3263-3273.
Feldman, Y. "Time Domain Dielectric Spectroscopy: An Advanced Measuring System" *Rev. Sci. Instrum.* (1996) vol. 67, No. 9, pp. 3208-3216.
Feldman, Y. D. et al. "Time Domain Dielectric Spectroscopy. A New Effective Tool for Physical Chemistry Investigation" *Colloid & Polymer Science* (1992) vol. 270, No. 8, pp. 768-780.
General Linear Least Squares in "Numerical Recipes in C: The Art of Scientific Computing" *Cambridge University Press. Programs* (1988) Chapter 15, pp. 671-681.
English translation and Statement of Accuracy of Translation of Abstract and description of DE 44 46 346 dated Jun. 27, 1996.

* cited by examiner

DEVICE AND METHOD FOR MEASURING A PROPERTY OF LIVING TISSUE

CROSS REFERENCE TO RELATED APPLICATIONS

This application claims the priority of international patent application PCT/CH03/00795, filed 2 Dec. 2003, the disclosure of which is incorporated herein by reference in its entirety.

TECHNICAL FIELD

The invention relates to a device for measuring a property of living tissue, in particular the glucose level of the tissue, and a method for doing the same.

BACKGROUND ART

It has been known that the glucose level in living tissue can be measured non-invasively by applying an electrode arrangement to the skin of a patient and measuring the response of the electrode arrangement to a suitable electric signal. Such a technique is described in WO 02/069791, the disclosure of which is enclosed herein in its entirety.

This type of device is equipped with an electrode arrangement for being applied to the specimen and a voltage-controlled oscillator as a signal source for generating an AC voltage in a given frequency range. The AC voltage is applied to the electrode arrangement. The response of the electrode arrangement, such as a voltage over the electrode arrangement depending on the dielectric properties of the tissue, is fed to a processing circuitry.

Even though this device is well able to monitor glucose, it needs careful calibration and must be operated under well-defined conditions in order to yield results of high accuracy.

The device of WO 02/069791 is one example of a device for measuring a parameter of living tissue. Similar types of devices can be used to measure other properties of the tissue that affect its response to an electric AC field; such as its dielectric constant, or an ion concentration.

Devices of this type should have high accuracy. In addition, in portable devices, low power consumption and low power supply voltages are desired.

DISCLOSURE OF THE INVENTION

Hence, in a first aspect of the invention, it is an object to provide a device of this type having low supply voltage.

Now, in order to implement this and still further objects of the invention, which will become more readily apparent as the description proceeds, a device according to claim 1 is used.

In the device according to this aspect of the invention, the voltage-controlled oscillator (VCO) comprises at least one voltage-controlled amplifier the gain of which can be set by a gain control signal. The VCO further comprises at least one tank circuit with a voltage-controlled capacitor determining a frequency of operation of the VCO. The device is adapted to control the gain control signal for increasing the gain when the DC-voltage over the voltage-controlled capacitor(s) is close to zero.

This makes it possible to operate the voltage-controlled capacitor with DC-voltages close to zero where its loss becomes high, thereby allowing to generate a wide range of frequencies with an only a moderate supply voltage and power consumption.

In a second aspect of the invention, it is an object of the invention to provide a device of the type mentioned above that allows an accurate measurement with simple circuitry.

This second aspect is achieved with the device of claim 7.

In a device according to this aspect, the processing circuitry comprises at least one diode for rectifying an AC input voltage and generating a rectified signal as well as an integrator for smoothing the same. The rectified, smoothed signal (or a signal derived therefrom) is fed to an A/D-converter and converted to a digital value. This digital value will depend on, but not be proportional to, the AC amplitude of the input voltage. Hence, it is converted to a signal value substantially proportional to the AC amplitude of the input voltage, e.g. by means of a calibration function or a lookup table. The wording "substantially proportional" is to designate that the signal value is more proportional to the AC amplitude than the digital value and can be used, at least in approximation, for calculations that require values exactly proportional to the AC amplitude.

In this manner, the analog circuitry is simplified without loss of accuracy. In particular, the analogue circuitry does not need to provide a signal that is exactly proportional to the AC amplitude of the input voltage.

In a second aspect of the invention, it is an object of the invention to provide a device of the type mentioned above, as well as a corresponding method of measurement, that allow an accurate measurement that efficiently exploits the available data.

This second aspect is achieved with the device of claim 14 and the method of claim 29.

In this aspect of the invention, an AC voltage of a series of frequencies $f_i$ is generated and applied to the specimen via the electrode arrangement. A corresponding series of measurement values $m_i$ at each of the frequencies $f_i$ is determined. Each measurement value $m_i$ depends on dielectric properties of the specimen at the corresponding frequency. A function $M(f, b_0, \ldots, b_K)$ with parameters $b_1$ to $b_K$ is fitted to the measurement values $m_i$ at their given frequencies $f_i$, or through values derived therefrom, thus determining the parameters $b_1$ to $b_K$. At least part of the parameters $b_1$ to $b_K$ can then be used for determining the desired property, e.g. using calibration data from earlier calibration measurements.

Since the involved fitting process exploits information from all used measurement values and inherently compensates for the effects of statistical fluctuations, the results obtained in this way have good accuracy.

In a third aspect of the invention, it is an object to provide a device of the type mentioned above that allows an accurate measurement.

This second aspect is achieved with the device of claim 19.

This aspect is based on the finding that an asymmetric design of the outer electrode provides a stronger, more reliable signal.

In a last aspect of the invention, it is an object to provide a device of the type mentioned above with high physiological compatibility.

This last aspect is achieved by the device of claim 22, where all through-contacts to the electrodes are covered with a biologically inert material. It has been found that though-contacts are a general source of noxious or allergenic substances. Hence, by covering the through-contacts, the biocompatibility of the device can be increased.

It must be noted that the features of the devices according to the various aspects can be used individually or in combination.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
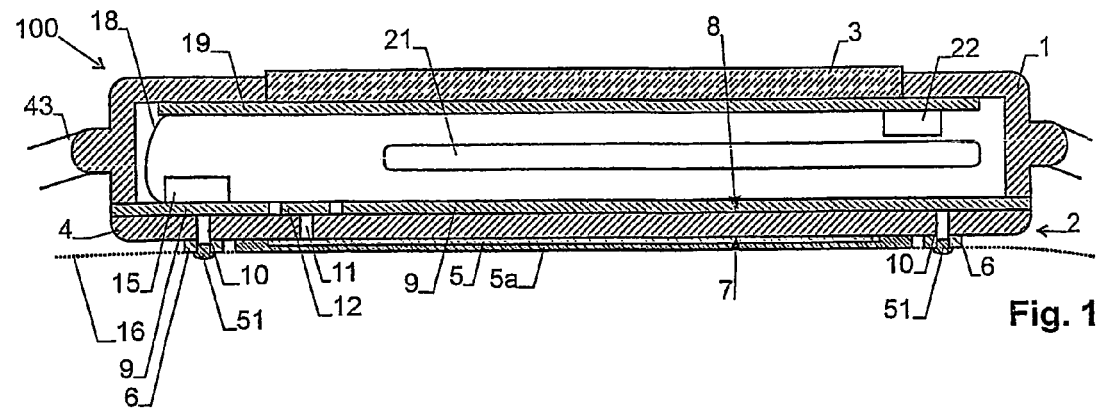
FIG. 1 is a cross section of a device for measuring a glucose level.

Basic Setup of the Device:

FIG. 1 shows a cross section of a device 100 for measuring a subjects's glucose level. It must be noted, though, that the same type of device can be measure any other parameter of living tissue that affects the response of the tissue to an applied electric AC field as mentioned above. Apart from the glucose level, such a property can e.g. be an electrolyte level of the tissue.

The device of FIG. 1 comprises a housing 1 closed on one side by an electrode plate 2. A display 3 is located opposite electrode plate 2. Electronic circuitry is arranged between electrode plate 2 and display 3.

Electrode plate 2 comprises a flat, electrically insulating substrate 4. A strip electrode 5 covered by an insulating layer 5a and an outer, annular electrode 6, which encloses strip electrode 5 at least partially or fully, are arranged on an outer side 7 of insulating substrate 4. An inner side 8 of insulating substrate 4 is covered by a ground electrode 9. A plurality of through-contacts 10 connect outer electrode 6 to ground electrode 9. A further through-contact 11 connects one end of strip electrode 5 to a contact pad 12 arranged on inner side 8.

A first temperature sensor 15 is mounted to ground electrode 9 in direct thermal contact thereto. The large number of through-contacts 10 ensures that ground electrode 9 closely follows the temperature of outer electrode 6 and therefore the temperature of the specimen, the surface of which is indicated by a dotted line 16.

Leads or springs 18 are provided to connect ground electrode 9, contact pad. 12 and first temperature sensor 15 to the electronic circuitry arranged on a printed circuit board 19 forming an assembly of electronic components. Printed circuit board 19 is advantageously arranged on a side of the device that is substantially opposite to the side of electrode plate 2. A battery 21 for powering the circuitry is arranged between printed circuit board 19 and electrode plate 2.

A second temperature sensor 22 is arranged on printed circuit board 19 and in direct thermal contact thereto.

The circuitry of device 100 can be the one described in WO 02/069791. An other possible circuit is, however, shown in the block circuit diagram of FIG. 2. It comprises a voltage-controlled oscillator (VCO) 31 as a signal source for generating a sine wave signal $V_{VCO}$ or another periodic signal of selectable frequency ω. This signal is fed to an amplifier 32, the output of which is connected via a resistor R1 to a signal point 34 and to a first input u1 of a measuring circuit 37. In addition, the output of amplifier 32 is fed directly to a second input u2 of measuring circuit 37. A resonant circuit 35 comprising an inductance L and a capacitor C in series is connected between signal point 34 and ground.

The operation of measuring circuit 37 will be further described below. Its output, which is e.g. the amplitudes and/or relative phase of the AC-voltages at inputs u1 and u2, is fed to a microprocessor 38, which also controls the operation of VCO 31.

Microprocessor 38 further samples the first and second temperature signals T1, T2 from first and second temperature sensors 15, 22. It also controls display device 3, an input device 40 with user operable controls, and an interface 41 to an external computer. A memory 42 is provided for storing calibration parameters, measurement results, further data as well as firmware for microprocessor 38. At least part of memory 42 is non-volatile.

Figure 2:
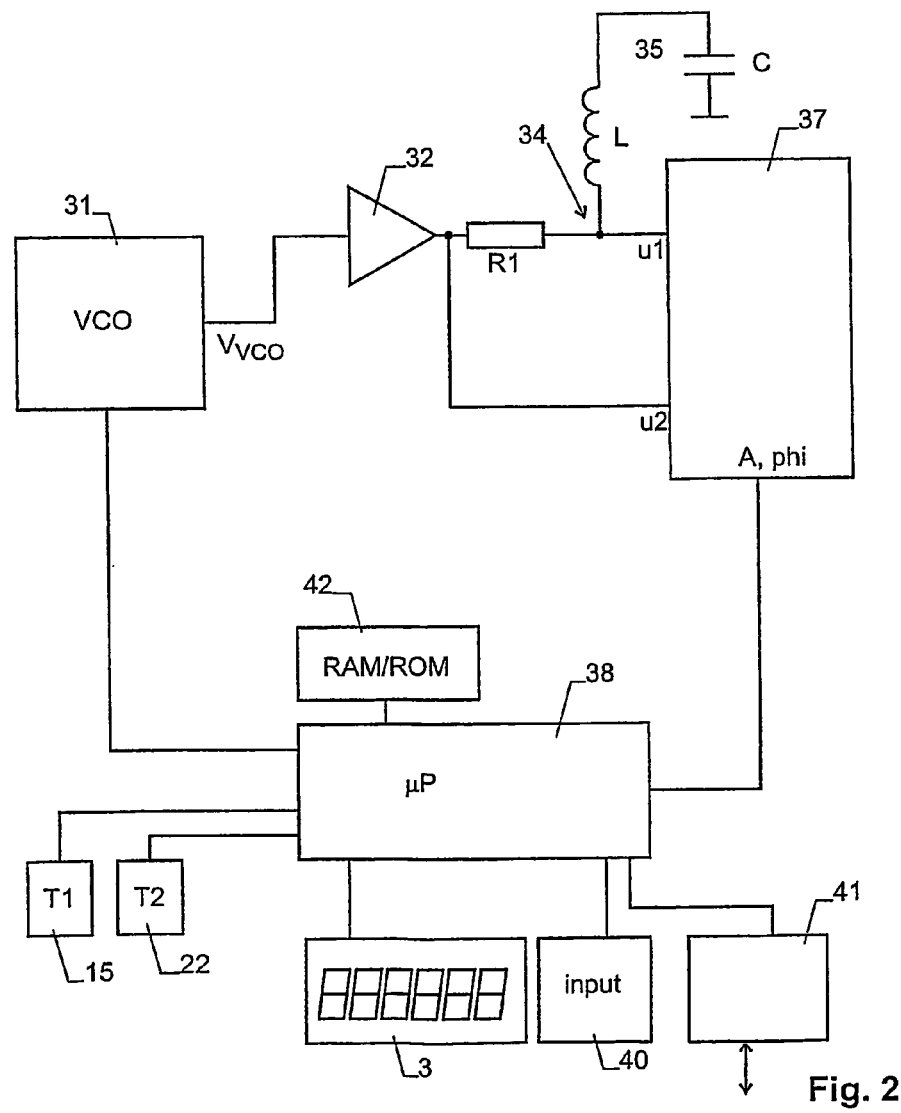
FIG. 2 is a block circuit diagram of the device of FIG. 1.

Inductance L of the device of FIG. 2 can be generated by a coil and/or by the leads and electrodes of capacitor C. Its value is generally known with reasonable accuracy.

Capacitor C of the device of FIG. 2 is formed between strip electrode 5 and outer electrode 6 and is used for probing the specimen. For this purpose, the electrodes are arranged on the skin 16 of the subject as shown in FIG. 1.

For a good and permanent contact with the subject's skin, the device is advantageously worn on an arm or leg and provided with a suitable holder or wrist band 43.

In summary, the device shown in FIGS. 1 and 2 comprises:
a voltage-controlled oscillator for generating an AC voltage in a given frequency range,
an electrode arrangement comprising the electrodes 5 and 6,
processing circuitry including the elements 31-33, 37, 38 for measuring the response of the electrode arrangement to an electrical signal and deriving the glucose level or some other parameter therefrom.

In addition, it can comprise at least two temperature sensors 15, 22, the signals of which depend in different manner on the skin temperature of the body and on the environmental temperature. One or, advantageously, both these temperatures can be to be taken into account when determining the glucose level.

Method of Operation:

The basic principle of operation of the device is described in WO 02/069791.

To measure the concentration of glucose in the body fluid of the patient, microprocessor 38 can e.g. initiate a measurement cycle consisting of a frequency sweep of VCO 1. The sweep should start at a frequency $f_{max}$ above the expected resonance frequency f0 of the resonant circuit 35 and extend to a frequency $f_{min}$ below resonance frequency f0 (or vice versa). During this sweep, the electrical properties of the resonant circuit will change. The amplitude determined by measuring circuit A will fall to a minimum A0 at a characteristic frequency f0, as described in WO 02/069791. Similarly, the phase shift phi will cross zero.

Microprocessor 38 measures A0 and/or f0, or some other parameter(s) descriptive of the frequency response of the device, as input values describing the physiological state of the subject's blood, body liquids and tissue. In addition to the input values of A0 and/or f0, microprocessor 38 measures the temperature values T1 and T2 as further input values. Using suitable calibration data, the glucose level can be derived from these input values.

Such calibration data can be determined from calibration measurements over a range of input values in straightforward manner using methods known to the person skilled in the art.

In general, microprocessor 38 will use a formula of the type $$g = F(s_1, s_2, \ldots, s_N, a_0, a_1, \ldots a_M) \tag{1}$$

for determining the glucose level g (or a parameter indicative thereof) from N measured input values $s_1, s_2, \ldots, s_N$ (N >0), where the function F has $M+1$ parameters $a_0, a_1, \ldots a_M$ (M≧0), at least some of which have to be determined in the calibration measurements.

The measured input values $s_i$ are e.g. values directly or indirectly derived from the amplitude A0, the corresponding frequency f0, and the temperatures T1, T2. The input values can e.g. be the most recent values measured or they can be a time average or a median over a given number of recent measurements. Possible input values are discussed in the section "Further processing of the raw signals" below.

The function F can be empirical or it can be based at least partially on a model describing the physical nature of the mechanisms involved.

Assuming that the relation between the glucose level g and the measured values $s_i$ is linear at least on approximation, we have $$g + a_0 + a_1 \cdot s_1 + a_2 \cdot s_2 + \ldots a_N \cdot s_N \tag{2a}$$

with M=N.

Equation (2a) has the advantage of being linear in the input values $s_i$ as well as the parameters $a_j$, which simplifies calibration as well as evaluation. More refined models can, however, be used as well.

In order to determine the parameters $a_0, a_1 \ldots, a_N$, a series of at least N+1 calibration measurements has to be carried out, each calibration measurement comprising a determination of the input values $s_j$ and a reference glucose level g measured by conventional means, e.g. an invasive method.

In a most simple approach, the parameters $a_i$ can then be obtained from a conventional least-squares fitting algorithm that varies the parameters $a_i$ in order to find a best match of equations (2) or (2a) to the calibration measurements. Suitable algorithms are known to a person skilled in the art and are e.g. described by Press, Teukolsky, Vetterling and Flannery in "Numerical Recipes in C", Cambridge University Press, $2^{nd}$ edition, 1992, Chapter 15.

Once the parameters $a_i$ are known, the glucose level g can be determined from equations (2) or (2a) based on the measurement of the input values $s_j$.

Re-calibration of at least part of the parameters may be advisable at regular intervals or after a displacement of device 100 in respect to the specimen.

In the following, various advantageous aspects of the present device are described in more detail.

Voltage-Controlled Oscillator:

In principle, various designs of voltage controlled oscillators are suited for being used in the present device, such as the one shown in FIG. 9 of WO 02/069791. In the following, though, an advantageous embodiment of a voltage-controlled oscillator is described, which operates with low supply voltage, has low power consumption, can oscillate in a large frequency range and generates sine-wave signals with only little distortions.

Figure 3:
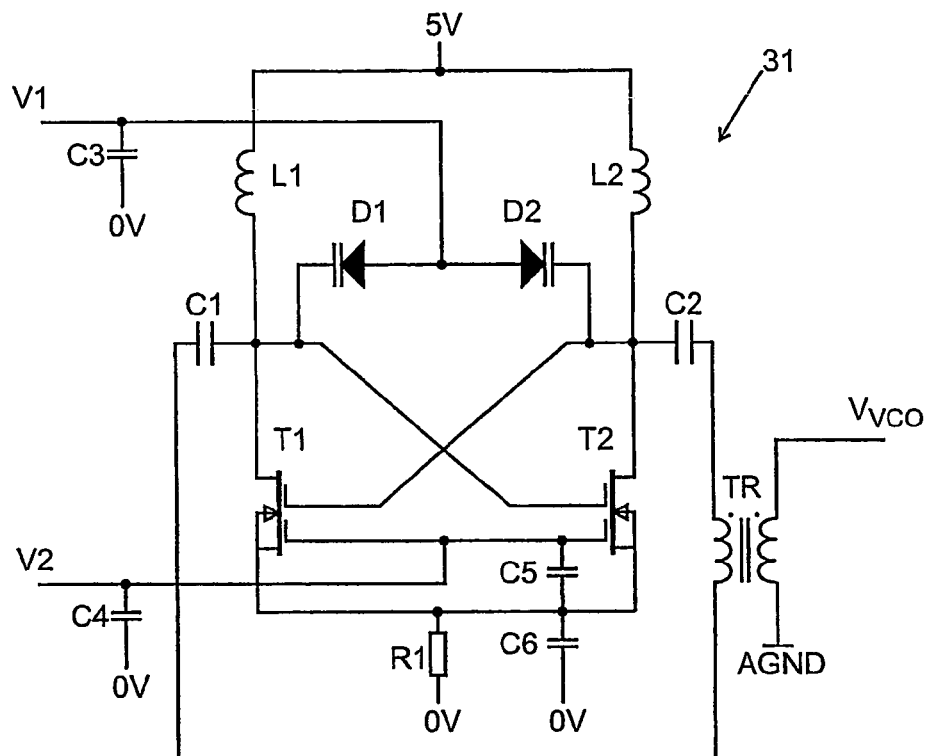
FIG. 3 is a circuit diagram of an advantageous embodiment of a voltage-controlled oscillator.

The voltage-controlled oscillator 31 of FIG. 3 comprises two symmetric tank circuits with inductances L1 and L2 and voltage-controlled capacitors (varactor diodes) D1, D2, respectively. The capacitance of the voltage-controlled capacitors D1, D2 is controlled by a frequency control voltage or frequency control signal V1. In addition, VCO 31 comprises two amplifiers each consisting of a dual-gate FET T1, T2. The gain of transistors T1, T2 is controlled by a gain control voltage or gain control signal V2. The components L1, D1, L2, D2 and T1, T2 are connected to oscillate at the resonant frequency of the tank circuits such that the voltages at the drains of T1, T2 are 180° out of phase. The drains of transistors T1, T2 and therefore the amplifier outputs are interconnected through capacitors C1, C2 arid the primary winding of a transformer TR. The secondary winding of transformer TR generates the output voltage $V_{VCO}$ in respect to analog ground AGND (which lies approximately at 2.5 Volts).

The frequency of VCO 31 can be selected via frequency control voltage V1, which can e.g. be generated by microprocessor 38. Typically, frequency control voltage V1 ranges between −10 and +5 Volts. However, when coming close to +5 Volts, the DC-voltage over D1 and D2 decreases and therefore the losses in D1, D2 increase. To compensate for these losses, the gain of the amplifiers is adjusted depending on the value of frequency control voltage V1, by increasing gain control voltage V2 and therefore the amplifier gain when the DC-voltage over voltage-controlled capacitors D1, D2 is close to 0.

Gain control voltage V2 may be generated by microprocessor 38. For example, microprocessor 38 can access calibration data in RAM/ROM 42 that gives, for each value of frequency control voltage V1, a suitable value of gain control voltage V2 or of a derivative thereof.

Advantageously, gain control voltage V2 is generated by a feedback loop that monitors the amplitude of output voltage $V_{VCO}$ or the signal at second input u2 of measuring circuit 37 and controls gain control voltage V2 to keep the amplitude constant. This will again lead to an increase in gain control voltage V2 when the DC-voltage over voltage-controlled capacitors D1, D2 comes close to 0.

Controlling voltage V2 in a feedback loop has the advantage that the output voltage is kept substantially constant even if the operating parameters of VCO 31 vary e.g. depending on temperature and/or circuit age. This is particularly important if measuring circuit 37 is designed for optimum performance over a certain voltage range only, and it ensures that nonlinearities of the response of the body to the applied electric field do not affect the measured signals.

The feedback loop for controlling V2 can be implemented using analog circuitry or with the aid of microprocessor 38. Using microprocessor 38 is advantageous because the circuit design is simplified. However, care must be taken that the implementation of the feedback loop does not unnecessarily increase the power consumption of the device.

Hence, an advantageous implementation of the feedback loop should avoid unnecessarily long operation of the VCO in order to find an appropriate value of V2. As mentioned above, microprocessor 38 can initiate a measurement cycle consisting of a frequency sweep of VCO 31. The sweep e.g. starts at a frequency $f_{max}$ and extends to a frequency $f_{min}$ and consists of repetitive measurements at a given series of frequencies $f_i$. In an advantageous embodiment, RAM/ROM 42 holds calibration data that allows to calculate, for each frequency $f_i$, the derivative $d(f_i) = dV2/df|_{f=f_i}$. Using this data, the following steps are taken to control the value of voltage V2:

In the first measurement cycle at frequency $f_1 = f_{max}$, the the value of V2 is varied by microprocessor 38 until voltage u2 is at a given value $u2_{opt}$ of e.g. 500 mV. The corresponding value of V2 is $V2(f_1)$.

In the second measurement cycle, the value of $V2(f_2)$ is calculated from $V2(f_1)$ by linear extrapolation using the derivative $d(f_1)$ (or $d(f_2)$ or a value between $d(f_1)$ and $d(f_2)$), e.g. $V2(f_2) = V2(f_1) + (f_1 - f_2) \cdot d(f_1)$.

In subsequent measurement cycles, $V2(f_{i+1})$ is calculated again by linear extrapolation from $V2(f_i)$, but the linearly extrapolated value is corrected by a correction, the value of which depends on if voltage u2 at frequency $f_i$ was above or below the desired value $u2_{opt}$. If voltage u2 at frequency $f_i$ was above $u2_{opt}$, the correction of V2 ($f_{i+1}$) is aimed to decrease voltage u2 at frequency $f_{i+1}$ and vice versa. For example, the relation V2($f_{i+1}$)=V2($f_i$)+k≶($f_i$−$f_{i+1}$)·d($f_i$) can be used for k either being 9/8 or 7/8 depending on the comparison of u2 with $u2_{opt}$ at frequency $f_i$, or V2($f_{i+1}$)=k'·(V2($f_i$)+($f_i$−$f_{i+1}$)·d($f_i$)) with k' being slightly above or below 1. This ensures that voltage u2 remains within a certain range around its optimum value $u2_{opt}$.

Hence, in general, in at least some of the measurement cycles i, a comparison of the output voltage of VCO 31 (or, equivalently, a voltage derived therefrom, such as voltage u2) with an optimum value ($u2_{opt}$) is carried out. The voltage V2 of a next measurement cycle i+1 is then corrected depending on the result of the comparison.

Instead of, or in combination with, a feedback loop for voltage V2, RAM/ROM 42 can hold temperature dependent calibration data for calculating a suitable value of voltage V2 at different frequencies and temperatures, and the temperature measured by temperature sensor 22 can be used to select the appropriate calibration data.

The symmetric design of VCO 31 with two amplifiers T1 and T2 and two tank circuits L1, D1 and L2, D2 operating at a phase shift of 180° and the fact that the output voltage $V_{VCO}$ is derived from the voltage drop over the outputs of the amplifiers lead to a sine signal with very low distortions. This is of particular importance if the device is to operate over a frequency range of more than 1:2. Depending on the design of measuring circuit 37, higher harmonics would otherwise give rise to additional signals leading to erroneous results.

A typical frequency range of the voltage-controlled oscillator as shown in FIG. 3 is 20 to 60 MHz for a frequency control voltage V1 of +5 to −10 Volts. The value of gain control voltage V2 is chosen to be approximately +4 Volts for V1 close to +5 Volts and +3 Volts for V1 much smaller than +5 Volts.

As can be seen from FIG. 3, both control voltages are smoothed by capacitors C3, C4, which act as filters to block any frequencies in the operating range of VCO 31, thereby making the oscillator signal more sinusoidal. For the same purpose, the gates connected to gain control voltage V2 are connected to the sources of the FETs by means of a filter capacitor C5. In addition, and again for the same purpose, the resistor R1 connected between 0V and the sources of transistors T1, T2 and acting as an approximate current source is arranged parallel to a capacitor C6, which again suppresses any oscillations of the resistor voltage at the range of frequencies of VCO 31.

Measuring Circuit 37:

In general, measuring circuit 37 can be any circuit that is able to measure the absolute or relative AC amplitudes of the signals at the inputs u1 and u2.

Figure 4:
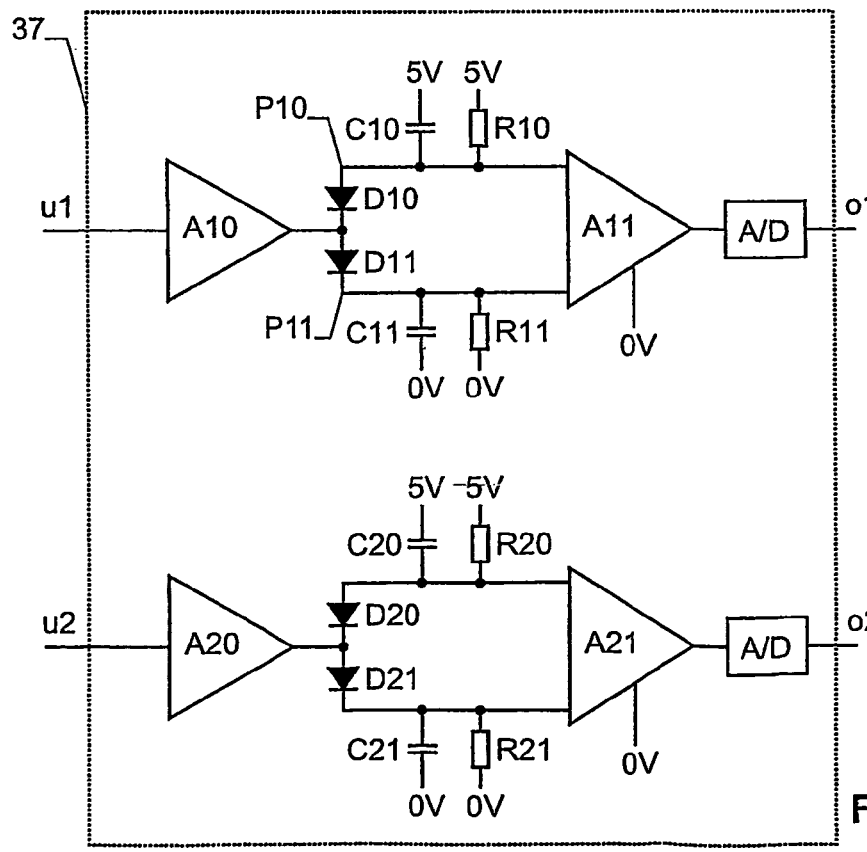
FIG. 4 is a circuit diagram of an advantageous embodiment of a measuring circuit.

An advantageous embodiment of the measuring circuit is shown in FIG. 4. It comprises two identical channels for processing the signals at the two inputs u1, u2. In the following, therefore, only the first channel for input u1 is discussed.

The signal at first input u1 is fed to an amplifier A10, the output of which is applied to two diodes D10, D11. Each diode generates a rectified signal at point P10 or P11, respectively. The rectified signal is connected to a capacitor C10 or C11 and a resistor R10 or R11, respectively, which act as an integrator or low pass filter and only pass frequencies much lower than the oscillator frequency f, thereby smoothing the rectified signals. Upper diode D10 is in series to upper filter C10, R10, and upper filter C10, R10 is connected to a first voltage (e.g. +5V). They generate a voltage at point P10 that depends on the minimum value of the AC signal. Lower diode D11 is in series to lower filter C11, R11, and lower filter C11, R11 is connected to a second voltage (e.g. 0V). The second voltage is lower than the first voltage. They generate a voltage at point P11 that depends on the maximum value of the AC signal.

Assuming that the voltage at input u1 is $$U(t)=U_0+x \cdot \sin(2\pi f t+\phi), \quad (3)$$

the voltage at point P10 after upper diode D10 is therefore $k \cdot (U_0-x)+u_d$, wherein k is the gain of amplifier A10 and $u_d$ is the forward voltage of diode D10 at the given frequency and temperature, while the voltage at point P11 after lower diode D11 is $k \cdot (U_0+x)-u_d$.

The voltages at points P10 and P11 are fed to an instrumental amplifier A11, which yields, at its output a voltage equal to or proportional to the difference of the voltages at its input. An A/D-converter is used to convert this voltage to a digital value o1. The digital value is proportional to $u_d$−k·x assuming that the response of all devices is linear.

Figure 5:
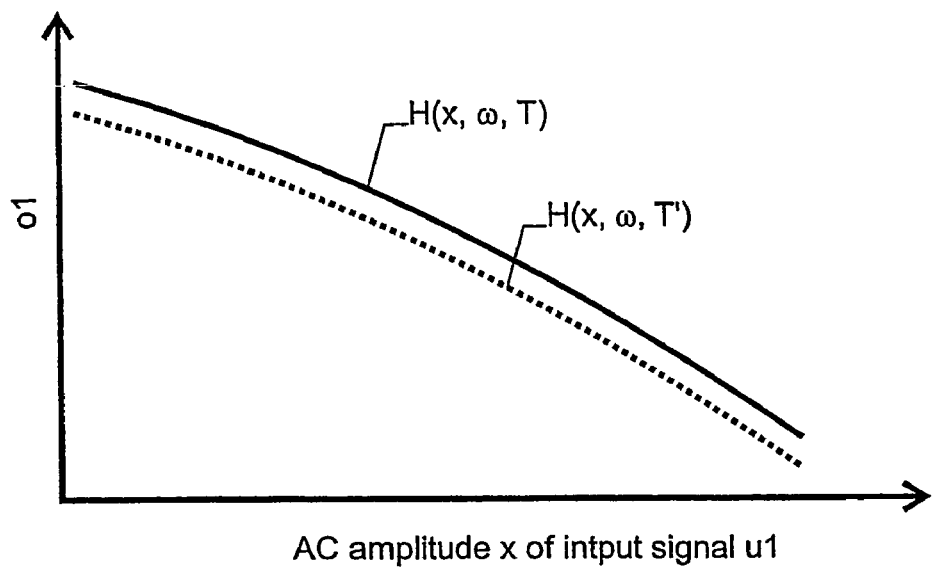
FIG. 5 is the dependence of the digital value at output of on the AC amplitude at input u1.

In general, taking into account that the response of some of the elements is not linear and that some parameters of the circuit, such as the forward voltage $u_d$, depend on temperature T, frequency ω and/or amplitude x, we have, for the digital value o1

$$o1=H(x, \omega, T), \quad (4)$$

where the response function H is qualitatively depicted in FIG. 5 for two different temperatures T and T'.

In a further processing step, a value proportional to the AC-amplitude x is required. Hence, microprocessor 38 is used for calculating the inverse of function H. For this purpose, the response function H can be determined in calibration measurements and its inverse can be stored as calibration data, e.g. in a table in RAM/ROM 42 for a plurality of temperatures T, frequencies f and AC amplitudes x. For each measurement, microprocessor 38 determines the digital value o1 as well as the temperature T (e.g. using second temperature detector T22) and the current frequency 107 (which it knows because it controls the operation of VCO 31 by means of frequency control voltage V1). Once the values of o1, ω and T are known, the value of x can be determined by interpolation from the table stored in RAM/ROM 42.

Instead of using a separate temperature detector T22, the temperature can also be determined from the temperature-dependent forward voltage $u_D$ of one or both of the diodes D10, D11. For this purpose, VCO 31 is switched off, in which case the digital value o1 is approximately equal to $2 \cdot u_D$ (where $u_D$ is the forward voltage at frequency 0 and dependent on temperature T).

Instead of using two diodes D10, D11, only a single diode and its corresponding resistor C11 and R11 would suffice, in which case instrumental amplifier A11 or A21 can be dispensed with or be replaced by a simple amplifier. The circuitry of FIG. 1 has, however, the advantage of generating a twice as high signal. In addition, the symmetric design provides a more accurate result.

Further Processing of the Raw Signals:

For the following steps, we assume that the electrode arrangement 5, 6 is connected to the output of VCO 31 via a first non-zero impedance Z1 (in the embodiment of FIG. 2, we have Z1=R1, but Z1 may also be an inductive, capacitive or mixed impedance). Hence, the voltage at the electrode arrangement 5, 6 depends on the dielectric properties of the specimen to be measured as well as on the output voltage $V_{VCO}$ from VCO 31. The AC-voltage at input u1 is derived from or equal to the voltage at the electrode arrangement 5, 6 and therefore also depends on the property of the specimen to be measured as well as, linearly, on the output voltage $V_{VCO}$ from VCO 31.

The input u2 is connected via a second impedance Z2 to the output of VCO 31. Z2 may be zero (as in the embodiment of FIG. 2) or non-zero. The AC-voltage at input u2 is, at least in good approximation, not dependent on the dielectric properties of the specimen to be measured, but it does depend linearly on the output voltage $V_{VCO}$ from VCO 31.

As described in WO 02/069791, a relative amplitude A between the AC voltages at inputs u1 and u2 is preferably used for further processing because such a relative amplitude is not dependent on the absolute amplitude of the output voltage $V_{VCO}$ of VCO 31. This relative amplitude A is $$A = x1/x2, \quad (5)$$

where x1 is the AC amplitude at input u1 and x2 is the AC amplitude at input u2. Equivalently, the reciprocal value x2/x1 can be used.

As mentioned above, microprocessor 38 can initiate a measurement cycle consisting of a frequency sweep of VCO 1. The sweep should start at a frequency $f_{max}$ above the expected resonance frequency f0 of the resonant circuit 35 and extend to a frequency $f_{min}$ below the resonance frequency f0. During this frequency sweep, repetitive measurements of the values x1 and x2 are carried out at a given series of frequencies $f_i$ using the circuitry described above. In each measurement i, at least one measurement value $m_i$ is determined. Typically, several hundred measurements are carried out in each measurement cycle.

The measurement values $m_i$ are, in general, a function g of one or both amplitudes x1 and x2:

$$m_i = g(x1_i, x2_i), \quad (6)$$

where $x1_i$ and $x2_i$ are the values of x1 and x2 measured in measurement i at a frequency $f_i$. Preferably, for the reasons mentioned above, $m_i$ should be derived from the relative amplitude A only, i.e. from the ratio of the amplitudes x1 and x2, i.e.

$$m_i = G(x1_i/x2_i) \quad (7)$$

with G being any suitable function, including the identity function. For example, one of the following definitions for the measurement value $m_i$ can be used $$m_i = x1_i/x2_i - 1. \quad (8a)$$

or $$m_i = x1_i/x2_i. \quad (8b)$$

Figure 6:
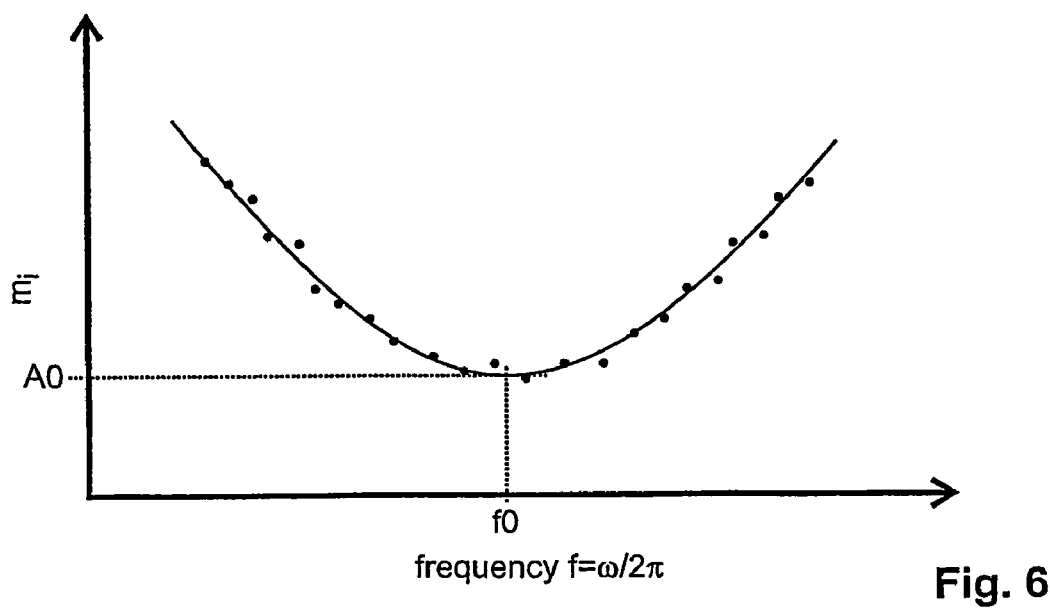
FIG. 6 shows a typical series of measurement values $m_i$ (dots) and a curve fitted through the values, FIG. 7 a bottom view of the device of FIG. 1.

Since the impedance of the resonant circuit 35 of FIG. 2 goes to a minimum at its resonance frequency f0, a typical series of measurement values $m_i$ looks as shown in FIG. 6.

Part of the input values $s_i$ of equations (1) and (2a) are to be derived from the measurement values $m_i$. In a simple approach, as it is described in WO 02/069791, a possible input value is the frequency $f_0$ where x1/x2 is smallest and the corresponding minimum value A0.

However, in an advantageous embodiment, the following procedure is used.

In a first step, a theoretical or empirical function M(f, $b_0, \ldots, b_K$) with parameters $b_1$ to $b_K$ is fitted through the points $m_i(f_i)$. Suitable algorithms are known to a person skilled in the art and are e.g. described by the standard textbook of Press et al. mentioned above.

In order to reduce the processing expense and/or to improve the accuracy of the measurement, the measured values $m_i$ can be preprocessed before fitting, e.g. by removing outliers or by numerical smoothing. In that case, the actual fitting process does not use the raw values $m_i$ and $f_i$ but values derived therefrom.

After determining the parameters $b_j$ in the fitting process, at least some of the input values $s_i$ are derived from at least some of the parameters $b_j$. For example, $s_1$ can be set to $b_0$, $s_2$ can be set to $b_1$ etc., or by through $b_K$ can be used to calculate the resonance frequency $f_0$ and the value of function M at $f_0$ and the two values obtained in this way can be used as input values $s_1$ and $s_2$, respectively.

In a simple embodiment, a polynomial of third degree is used for function M, i.e.

$$M(f, b_0, \ldots, b_K) = b_0 + b_1 \cdot f + b_2 \cdot f^2 + b_3 \cdot f^3 \quad (9)$$

is used. Polynomials of degree R with R>3 or R=2 can be used as well, but it has been found that polynomials of lower degree do not describe a possible asymmetry of the data sufficiently well, and the available data does not provide sufficient information for determining more than four parameters.

As known to a person skilled in the art and as described in chapter "General Linear Least Squares" in the book of Press et al. mentioned above, fitting a function that is linear in its parameters $b_j$, such as the one of equation (9), to a data set can be carried out by solving the matrix equation $$(A^T \cdot A) \cdot b = A^T \cdot m, \quad (10)$$

where, for the function of equation (9), A is the matrix $$A_{ij} = f_i^j, \quad (11)$$

b is the vector of the parameters $\{b_0 \ldots b_K\}$ and m the vector of the values $\{m_1 \ldots m_L\}$. In general, when function M takes the form $$M(f, b_0, \ldots b_K) = \sum_{k=0}^{K} b_k \cdot \chi_k(f) \quad (12)$$

with $\chi_k$ being arbitrary functions of frequency f, matrix $A_{ij}$ is given by $$A_{ij} = \chi_j(f_i) \quad (13)$$

(Equations (11) and (13) assume that the measurement errors of all measurements are equal. If not, the equations must be corrected as described in the textbook of Press et al., chapter 15.4. In the following, as well as in the claims, the simple form of equations (11) and (13) is used, but the application of error corrected formulae for $A_{ij}$ is deemed to be an equivalent thereof.)

As can be seen, matrix A does not depend on the measured values $m_i$ but only on the frequencies $f_i$. If the same frequencies $f_i$ are used in each sweep, matrix A as well as $(A^T \cdot A)$ and its inverse can be precalculated and stored in advance, thereby obviating the need for calculating them for each frequency sweep and taking computational load from microprocessor 38, which allows to increase the number of sweeps and/or to decrease power consumption. Preferably, $(A^T \cdot A)^{-1} \cdot A^T$ is precalculated and stored, but it is also possible to store any other suitable data describing the precalculated matrix A.

Electrode Design:

The geometry of the electrodes 5, 6 is selected such that the electric AC-field generated by them extends into the tissue to be measured. Advantageously, at least one of the electrodes of the capacitor is electrically insulated such that capacitor C attached to the body, which can be modeled as a resistive and capacitive load, results primarily a capacitive load, the capacitance and loss of which depend on the electrical properties (i.e. the response) of the specimen at the frequency of VCO 1.

The design of the electrodes 5, 6 of the present sensor can correspond to the one described in reference to FIGS. 2 and 4 of WO 02/069791, which description is enclosed by reference herein.

Figure 7:
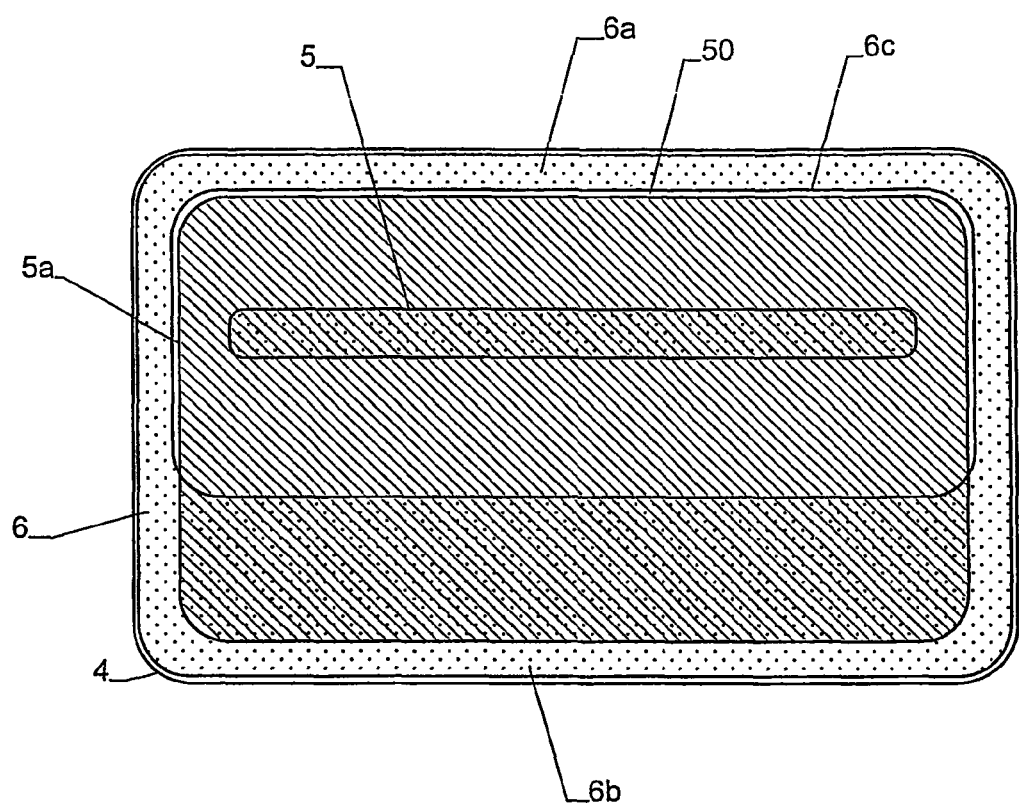

In an advantageous embodiment, though, an electrode arrangement as shown in FIG. 7 is used. In this figure, the hatched area corresponds to the area covered by insulating layer 5a, while the dotted areas correspond to the areas covered by electrodes 5 and 6.

As can be seen, outer electrode 6 is of elongate shape having two lateral sections 6a, 6b extending substantially parallel to strip electrode 5, wherein section 6b is wider than section 6a. An inner edge 6c of outer electrode 6 encloses a central area 50 of substantially rectangular shape. Strip electrode 5 is located substantially in the center of central area 50.

Insulating layer 5a covers substantially all of central area 50 as well as part of the wider lateral section 6b of outer electrode 6.

Any surface of an electrode that can come into contact with the specimen should be of gold or another noble metal for best biological compatibility. In the embodiment of FIG. 7, at least outer electrode 6 is advantageously covered by a gold layer.

For the same reason, at least those through-contacts 10 that are not covered by insulating layer 5a should be covered by glass, ceramics, plastics, a noble metal layer or any other biologically inert material. In the embodiment of FIG. 1, the through-contacts 10 are therefore covered by drops of glass 51.

Notes:

In the above description, the voltage over resonant circuit 35 was measured at input u1. It must be noted, though, that it would also be possible to measure another voltage or current that depends on the impedance of the electrode arrangement. In particular, it would be possible to measure the voltage drop over resistor R1 or inductance L instead of the voltage over resonant circuit 35.

In any case, the processing circuitry 37, 38 should measure a response of the electrode arrangement to the applied electric signal, i.e. the measured value should depend on the dielectric properties of the specimen at the electrode.

Furthermore, resonant circuit 35 might also be implemented as a capacitor parallel to an inductance instead of having the capacitor arranged in series to the inductance.

Finally, it must be noted that the electrode arrangement shown in FIGS. 1 and 7 is only one of various possible embodiments. For example, outer electrode 6 might be replaced by a part of the (metallic) housing 1 of device 100 extending to the electrode face of the device. In that case, metallic housing 1 would form part of the electrode arrangement.

While there are shown and described presently preferred embodiments of the invention, it is to be distinctly understood that the invention is not limited thereto but may be otherwise variously embodied and practiced within the scope of the following claims.

The invention claimed is:

1. A device for measuring a property of living tissue, in particular a glucose level of the tissue, said device comprising an electrode arrangement for application to the tissue, a signal source for generating an AC voltage at a series of frequencies in a given frequency range to be applied to said electrode arrangement, and processing circuitry comprising
measuring means for measuring a series of measurement values at the series of frequencies, each measurement value depending on dielectric properties of the tissue at one frequency,
fitting means for fitting a function $M(f, b_0, \ldots, b_K)$ with parameters $b_0$ to $b_K$ to the measurement values at their given frequencies, or to values derived from the measurement values at their given frequencies, and determining the parameters $b_0$ to $b_K$ thereby, and
means for using at least part of the parameters $b_0$ to $b_K$ for determining said property,
wherein said measuring processing circuitry comprises a measuring circuit having a first input for an input value dependent on said property and on said AC voltage and a second input for an input value dependent on said AC voltage but substantially independent of said property, wherein said measurement values are derived from a ratio between said first and said second input value.

2. A device for measuring a property of living tissue, in particular a glucose level of the tissue, said device comprising an electrode arrangement for application to the tissue, a signal source for generating an AC voltage at a series of frequencies in a given frequency range to be applied to said electrode arrangement, and processing circuitry comprising
measuring means for measuring a series of measurement values at the series of frequencies, each measurement value depending on dielectric properties of the tissue at one frequency,
fitting means for fitting a function $M(f, b_0, \ldots, b_K)$ with parameters $b_0$ to $b_K$ to the measurement values at their given frequencies, or to values derived from the measurement values at their given frequencies, and determining the parameters $b_0$ to $b_K$ thereby, and
means for using at least part of the parameters $b_0$ to $b_K$ for determining said property,
wherein said function $M(f, b_0, \ldots, b_K)$ is of the form $$M(f, b_0, \ldots, b_K) = b_0 + b_1 \cdot f + \ldots + b_3 \cdot f^R,$$

in particular with R=3.

3. A device for measuring a property of living tissue, in particular a glucose level of the tissue, said device comprising an electrode arrangement for application to the tissue, a signal source for generating an AC voltage at a series of frequencies in a given frequency range to be applied to said electrode arrangement, and processing circuitry comprising
measuring means for measuring a series of measurement values at the series of frequencies, each measurement value depending on dielectric properties of the tissue at one frequency,
fitting means for fitting a function $M(f, b_0, \ldots, b_K)$ with parameters $b_0$ to $b_K$ to the measurement values at their given frequencies, or to values derived from the measurement values at their given frequencies, and determining the parameters $b_0$ to $b_K$ thereby, and
means for using at least part of the parameters $b_0$ to $b_K$ for determining said property,
wherein said function $M(f, b_0, \ldots, b_K)$ is of the form $$M(f, b_0, \ldots b_K) = \sum_{k=0}^{K} b_k \cdot \chi_k(f)$$

and wherein said fitting means is adapted to store a precalculated matrix A and/or data derived from said precalculated matrix A for fitting a plurality of series of measurement values, wherein matrix $A=A_{ij}$ is defined by $$A_{ij}=\chi_j(f_i).$$

4. The device of claim 3, wherein said fitting means is adapted to store the matrix $(A^T \cdot A)^{-1} \cdot A^T$.

5. The device of claim 1,
wherein said electrode arrangement comprises a strip electrode for being placed against said body,
an outer electrode for being placed against said body, wherein said outer electrode comprises two lateral sections extending substantially parallel to and on opposite sides of said strip electrode, wherein a first of said sections is wider than a second of said sections.

6. The device of claim 5, further comprising an insulating layer covering said strip electrode and at least part of said first section of said outer electrode.

7. The device of claim 5, wherein said outer electrode is annular.

8. The device of claim 1,
wherein said electrode arrangement comprises
at least one electrode placed on an outer side of an electrically insulating substrate,
at least one through-contact extending through said substrate and connecting said at least one electrode,
wherein an outer side of each through-contact is covered by a physiologically inert material.

9. The device of claim 8, wherein the outer side of each through-contact is covered by a material selected from the group of glass, ceramics, plastics and a noble metals.

10. The device of claim 8, wherein said electrode arrangement comprises at least a first electrode for being brought into direct contact with said body and wherein a surface of said first electrode consists of noble metal.

11. The device of claim 10, wherein the surface of said first electrode consists of gold.

12. The device of claim 8, wherein said electrode arrangement is part of a resonant circuit, and in particular wherein a resonance frequency of the resonant circuit lies in the given frequency range.

13. The device of claim 12, wherein said electrode arrangement forms a capacitor and is arranged in series to or parallel to an inductance, wherein said capacitor and said inductance form said resonant circuit.

14. The device of claim 8, wherein said electrode arrangement is arranged on a flat substrate.

15. A method for measuring a property of living tissue, in particular a glucose level of the tissue, said method comprising the steps of
applying an electrode arrangement to the tissue,
generating an AC voltage at a series of frequencies in a given frequency range and applying the AC voltage to said electrode arrangement,
measuring a series of measurement values at the frequencies, each measurement value depending on dielectric properties of the tissue at one frequency,
fitting a function $M(f, b_0, \ldots, b_K)$ with parameters $b_0$ to $b_K$ to the measurement values at their frequencies, or through values derived from the measurement values at their frequencies, and determining the parameters $b_0$ to $b_K$ thereby, and
determining said property by using at least part of the parameters $b_0$ to $b_K$,
measuring a first input value dependent on said property and on said AC voltage,
measuring a second input value dependent on said AC voltage but substantially independent of said property, and
deriving said measurement values from a ratio between said first and said second input value.

16. A method for measuring a property of living tissue, in particular a glucose level of the tissue, said method comprising the steps of
applying an electrode arrangement to the tissue,
generating an AC voltage at a series of frequencies in a given frequency range and applying the AC voltage to said electrode arrangement,
measuring a series of measurement values at the frequencies, each measurement value depending on dielectric properties of the tissue at one frequency,
fitting a function $M(f, b_0, \ldots, b_K)$ with parameters $b_0$ to $b_K$ to the measurement values at their frequencies, or through values derived from the measurement values at their frequencies, and determining the parameters $b_0$ to $b_K$ thereby, and
determining said property by using at least part of the parameters $b_0$ to $b_K$,
wherein said function $M(f, b_0, \ldots, b_K)$ is of the form $$M(f, b_0, \ldots, b_K) = b_0 + b_1 f + \ldots + b_3 f^R,$$

in particular with R=3.

17. A method for measuring a property of living tissue, in particular a glucose level of the tissue, said method comprising the steps of
applying an electrode arrangement to the tissue,
generating an AC voltage at a series of frequencies in a given frequency range and applying the AC voltage to said electrode arrangement,
measuring a series of measurement values at the frequencies, each measurement value depending on dielectric properties of the tissue at one frequency,
fitting a function $M(f, b_0, \ldots, b_K)$ with parameters $b_0$ to $b_K$ to the measurement values at their frequencies, or through values derived from the measurement values at their frequencies, and determining the parameters $b_0$ to $b_K$ thereby, and
determining said property by using at least part of the parameters $b_0$ to $b_K$,
wherein said function $M(f, b_0, \ldots, b_K)$ is of the form $$M(f, b_0, \ldots b_K) = \sum_{k=0}^{K} b_k \cdot \chi_k(f)$$

said method further comprising the steps of
storing a precalculated matrix A and/or data derived from said precalculated matrix A, wherein matrix $A=A_{ij}$ is defined by $A_{ij}=\chi_j(f_i)$,
using said precalculated matrix A and/or said data derived from said precalculated matrix A for fitting a plurality of series of measurement values.

18. The method of claim 17, comprising the step of storing the matrix $(A^T \cdot A)^{-1} \cdot A^T$.

* * * * *